United States Patent [19]

Tcheng et al.

[11] Patent Number: 4,836,035
[45] Date of Patent: Jun. 6, 1989

[54] SKIN FRICTION BALANCE

[75] Inventors: Ping Tcheng, Norfolk; Frank H. Supplee, Jr., Hampton, both of Va.

[73] Assignee: The United States of America as represented by the Administrator of the National Aeronautics and Space Administration, Washington, D.C.

[21] Appl. No.: 210,487

[22] Filed: Jun. 23, 1988

[51] Int. Cl.$^4$ ............................................. G01L 1/08
[52] U.S. Cl. ................................. 73/862.61; 73/147
[58] Field of Search ............... 73/147, 862.61, 861.73, 73/861.71, 862.04

[56] References Cited

U.S. PATENT DOCUMENTS 3,304,775  2/1967  Kistler .................................. 73/147
3,742,762  7/1973  Tomiyasu et al. ............... 73/861.73
4,604,903  8/1986  Tcheng et al. ......................... 73/147

Primary Examiner—Donald O. Woodiel
Attorney, Agent, or Firm—Harold W. Adams; John R. Manning; Charles E. B. Glenn

[57] ABSTRACT

A skin friction balance uses a parallel linkage mechanism to avoid inaccuracies in skin friction measurement attributable to off-center normal forces. The parallel linkage mechanism includes a stationary plate mounted in a cage, and an upper and lower movable plate which are linked to each other and to the stationary plate through three vertical links. Flexure pivots are provided for pivotally connecting the links and the plates. A sensing element connected to the upper plate moves in response to skin friction, and the lower plate moves in the opposite direction of the upper plate. A force motor maintains a null position of the sensing element by exerting a restoring force in response to a signal generated by a linear variable differential transformer (LVDT).

9 Claims, 4 Drawing Sheets

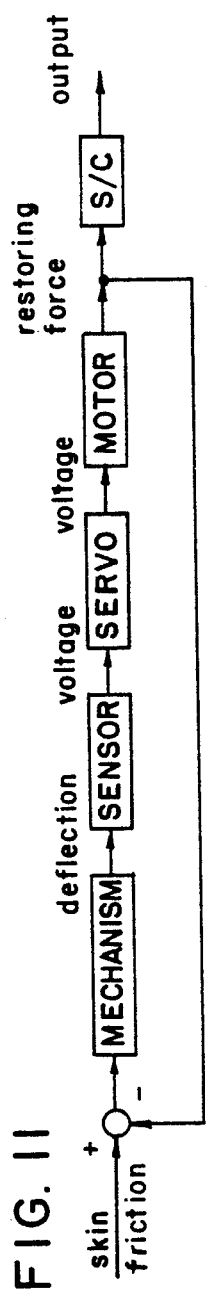
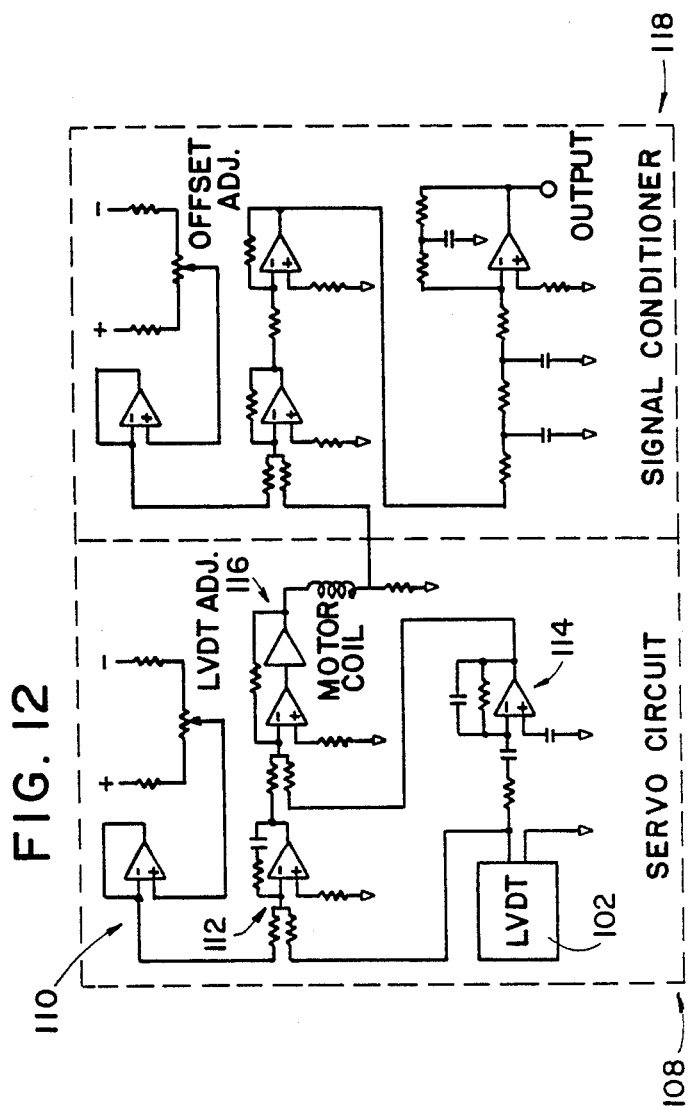
FIG. 11
FIG. 12

SKIN FRICTION BALANCE

ORIGIN OF THE INVENTION

The invention described herein was made by employees of the United States Government and may be used by or for the Government for governmental purposes without the payment of any royalties hereon or therefor.

BACKGROUND OF THE INVENTION

1. Field of the Invention

The present invention relates generally to skin friction force measuring devices and, more specifically, to a skin friction balance having a sensing element mounted on a parallel linkage mechanism.

2. Description of the Related Art

Skin friction balances are generally known. A skin friction balance is used to determine the skin friction drag component of the total drag acting on an aerodynamic body. A variety of balances have been devised to address certain problems which affect the accuracy of the skin friction measurement. In U.S. Pat. No. 2,935,870 to Lyons, a skin friction balance is described which avoids inaccuracies which result from acceleration forces. The apparatus of U.S. Pat. No. 2,935,870 includes a linear variable differential transformer having stationary coils and a movable core. The core is mounted to a central body which is movable relative to a stationary base when skin friction force acts upon a surface element attached to the central body. A counter-weight system prevents skin friction force measurements from being effected by linear and angular accelerations.

U.S. Pat. No. 3,304,775 to Kistler describes a skin friction gage for use in a high speed, high temperature environment, such as what is experienced by high Mach speed re-entry vehicles. A small sensing element constitutes a portion of the surface where it is desired to measure skin friction drag and is free to move relative to the surrounding area. Movement of the sensing element causes a corresponding motion of a differential capacitive pickoff. A change in differential capacitance produces a corresponding current through a coil mechanically attached to the pickoff and the sensing element. A force is created which opposes the outside forces which tend to cause displacement of the sensing element. Thus, measurement of the current is equivalent to measurement of the external drag force.

U.S. Pat. No. 4,240,290 to Montoya et al. describes a skin friction measuring device which uses a potentiometer, the power supply of which is varied in accordance with a variable resistor. An air stream passing over the surface of a friction plate causes displacement of the plate and deflection of flexural members supporting the friction plate.

U.S. Pat. No. 3,383,914 to MacArthur teaches a skin friction transducer which addresses the problem that inaccurate measurements result when the sensing element experiences pressure force normal to the sensing area. To solve the problem, fluid communication was provided between opposite sides of the sensing element to equalize pressure.

U.S. Pat. No. 4,604,903 to Tcheng et al. describes a skin friction balance which is capable of two-axis self-nulling. Skin friction forces were measured along two perpendicular axis by providing an L-shaped arm having a second arm pivotally connected to one end thereof. Two separate nulling devices were provided to keep a sensing element in the null position.

The above-described known devices are generally sensitive to off-center normal force and/or acceleration. Also, because most of the above are "open-loop" devices, accuracy is generally less than acceptable. Most open-loop designs require a larger than acceptable gap size between a balance case and the sensing element.

SUMMARY OF THE INVENTION

An object of the present invention is to provide a skin friction balance which is less sensitive to off-center normal forces.

Another object of the invention is to provide a skin friction balance which is less sensitive to acceleration forces.

Another object of the invention is to provide a skin friction balance which has a high degree of overall accuracy.

Yet another object of the invention is to provide a skin friction balance which minimizes the gap between the sensing element and the surrounding area of the aerodynamic body.

In a preferred embodiment of the invention, a skin friction balance includes a parallel linkage mechanism which includes a housing having two opposite sides, a stationary plate having two opposite sides and two opposite ends and being fixedly mounted by the two opposite ends between the two opposite sides of the housing, at least one link pivotally connected to each of the two opposite sides of the stationary plate at the center of each link, an upper movable plate pivotally connected to one end of each link, and a lower movable plate pivotally connected to the opposite end of each link. When the upper movable plate moves in one direction, the lower movable plate moves in the opposite direction due to the stationary plate and the pivotal connections between the plates and links. A sensing element is fixedly connected to the upper movable plate and is movable therewith in response to sensed skin friction. A linear variable differential transformer (LVDT) outputs a signal indicative of a position of the sensing element and has a body connected to the stationary plate and an armature movable in response to movement of the lower and upper movable plates. A motor has a magnet fixedly connected to the housing and coil windings which are fixedly connected to the lower movable plate. A control circuit processes the transformer signal and outputs a current to the motor at a level sufficient to maintain the sensing element in a null position. Thus, the level of current to the motor indicates the amount of skin friction.

These objects, together with other objects and advantages which will be subsequently apparent reside in the details of construction and operation of the apparatus and more fully hereinafter described and claimed, reference being had to the accompanying drawings forming a part hereof, wherein like reference numerals refer to like parts throughout.

BRIEF DESCRIPTION OF THE DRAWINGS

FIG. 11 is a block diagram of the control system for the FIG. 2 embodiment; and

FIG. 12 is an electrical schematic diagram of the control system of the FIG. 2 embodiment.

DETAILED DESCRIPTION OF THE PREFERRED EMBODIMENTS

Figure 1:
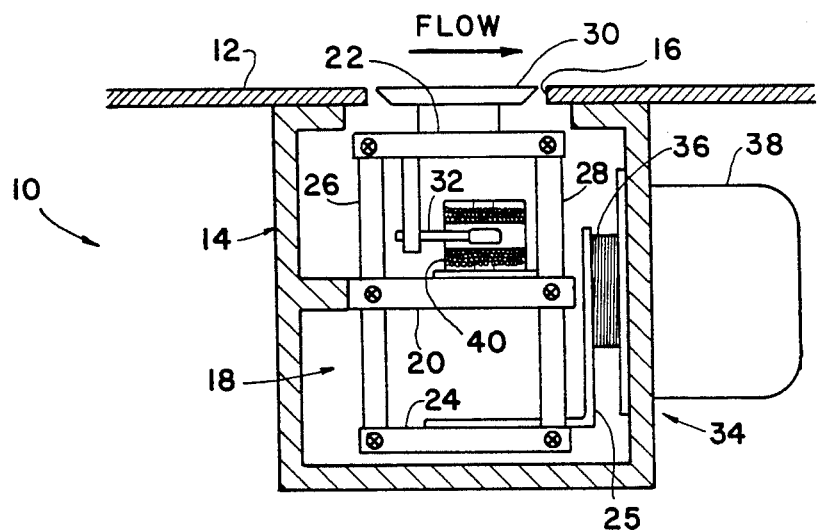
FIG. 1 is a schematic illustration of a first preferred embodiment of the present invention.

Referring to FIG. 1, a skin friction balance 10 according to the present invention is connected to the inside of an aerodynamic surface 12. A housing 14 of the skin friction balance 10 is connected to the inside of the aerodynamic surface 12 centrally behind an opening 16. The connection may be made by any conventional means. A parallel linkage mechanism 18 is connected to the housing 14 through a stationary plate 20 of the parallel linkage mechanism 18.

An upper moving plate 22 is maintained in a spaced apart, parallel relationship with lower moving plate 24 by means of three flexure links. Only links 26 and 28 are illustrated in FIG. 1. The third link is disposed on a side opposite links 26 and 28.

A sensing element 30 is connected to the upper moving plate 22. The upper moving plate 22 also carries an armature 32 of a displacement transducer 40.

A force motor 34 includes coil windings 36 which are fixedly connected to the lower moving plate 24 by bracket 25, and a permanent magnet 38 is disposed adjacent the coil windings 36 and is connected to the housing 14. The force motor 34 exerts a restoring force on the lower moving plate when skin friction force is experienced at the sensing element 30. A linear variable differential transformer (LVDT) 40 is used to measure the movement of the sensing element 30, which correlates to movement of the parallel linkage mechanism 18. The output from the LVDT 40 provides not only the error signal for the closed-loop servosystem and thus the current to the force motor 34 but also indirectly provides a damping effect required by the servomechanism.

The arrangement of the parallel linkage mechanism 18 provides insensitivity to off-center normal force caused by pressure gradients. Also, the balance 10 is made insensitive to background rectilinear vibrations and can sustain large transient loads during aircraft takeoffs and landings.

Figure 2:
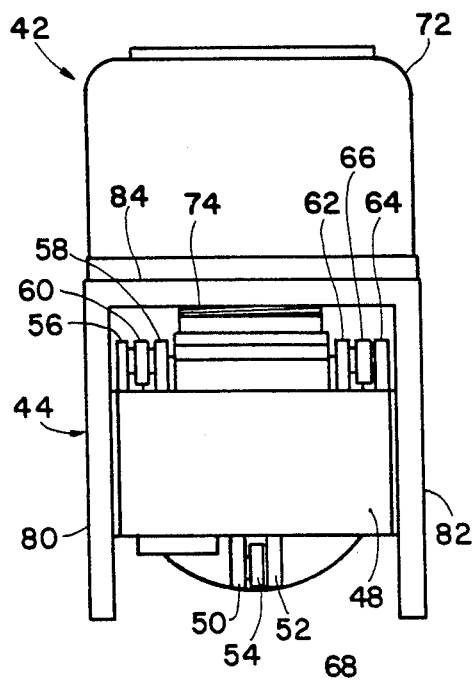
FIG. 2 is a rear view of a first preferred embodiment of the present invention.
Figure 3:
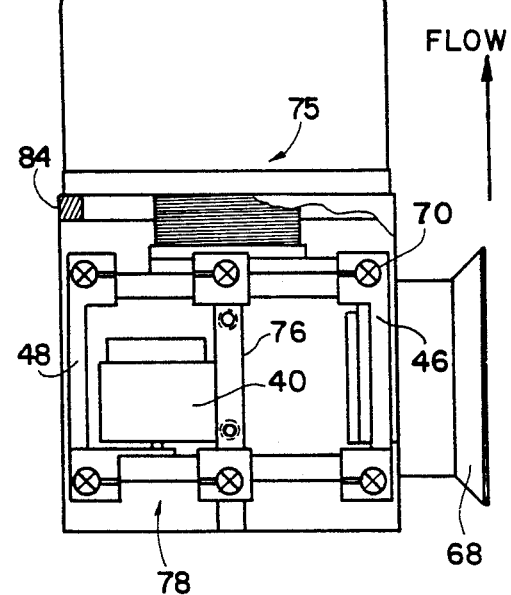
FIG. 3 is a side view, partially cut away, of the embodiment of FIG. 2.
Figure 4:
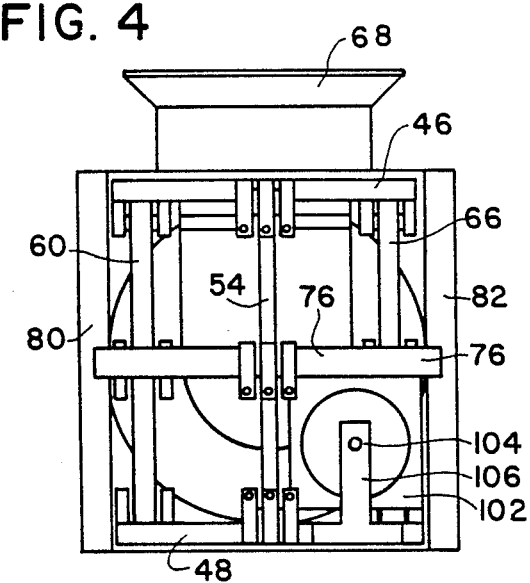
FIG. 4 is a bottom view of the embodiment of FIG. 2.

FIGS. 2, 3 and 4 are different views of a skin friction balance 42 which is substantially the same as the one schematically illustrated in FIG. 1. A cage 44 is used to house an upper moving plate 46 and a lower moving plate 48, each of which includes brackets 50 and 52 for pivotally connecting link 54. Brackets 56 and 58 pivotally connect link 60, while brackets 62 and 64 pivotally connect link 66. Sensing element 68 is connected to the upper moving plate 46 and moves in a direction opposite the lower moving plate 48.

All pivotal connections between the links 54, 60, and 66, and the brackets are made by flexure pivots 70 which are intended to minimize or eliminate friction between the various moving parts. Each link has three flexure pivots 70, each of which is made of a pair of crossed flexures of flat springs connected to two outer sections through an intermediate section. Each flexure pivot functions as a torsional spring when the intermediate section is twisted relative to the two outer ones. Since each flexure pivot has no contacting parts, a sustained oscillation can be achieved with a restoring moment being generated within the flexure pivots when the mechanism is disturbed.

A viscous force of the air flow is detected by the outer surface of the sensing element 68, which is to be disposed in an opening similar to the one schematically illustrated in FIG. 1. The sensing element has a convex profile and has a circular shape, preferably about 2 inches in diameter. The outer surface is machined to the contour of the area of the aerodynamic surface, such as a fuselage, in which it is located. The sensing element 68 is preferably separated from the surrounding area by an annular gap of about 0.010 inches. The sensing element 68 is concentric with the opening and is flush with the surrounding area.

The skin friction balance 42 illustrated in FIGS. 2-4 has components similar to those schematically illustrated in FIG. 1. For instance, a permanent magnet 72 is connected to a rear wall of the cage 44 adjacent coil windings 74, which are connected to the stationary plate 76. The entire parallel linkage mechanism 78 is housed inside the cube-shaped balance cage 44 which has two opposite side walls 80 and 82 and a rear wall 84. The cage 44 acts as a bracket for attaching and aligning the moving parts within a balance case (not shown in FIGS. 2-4). Also, the heavy permanent magnet 72 is mounted on the cage 44.

The force motor 75 is part of a servomechanism and includes coil windings 74 supported on the lower moving plate 48. The upper moving plate 48 supports sensing element 68. An LVDT 102 is supported on the stationary plate 76 and an armature 104 (FIG. 4) extends into the LVDT 102 from a support 106 connected to the lower moving plate 48. It should be noted that the armature 104 and the LVDT 102 can be arranged according to FIG. 4, or according to the schematic illustration of FIG. 1, in which the LVDT 40 is mounted on an upper side of the stationary plate 20 and the armature 32 is mounted on the upper moving plate 22. In either position, movement of the sensing elements (30 or 68) results in relative movement between the armature (32 or 104) and the LVDT (40 or 102). Thus, the LVDT is used to measure the movement of the sensing element. The output signal from the LVDT provides not only the error signal of the servomechanism but also indirectly the damping required by the servomechanism.

The permanent magnet (or pole piece) 72 of the force motor 75 is attached to the bottom wall 84 of the cage 44. The coil windings 74 of the force motor 75 are partially housed inside the magnet 72, and are mounted on the lower moving plate 48. The motor 75 is a type of commercially available mechanical shaker, modified to prevent direct physical contact between the coil windings 74 and the magnetic 72 in order to prevent frictional interference therebetween.

Figure 5A:
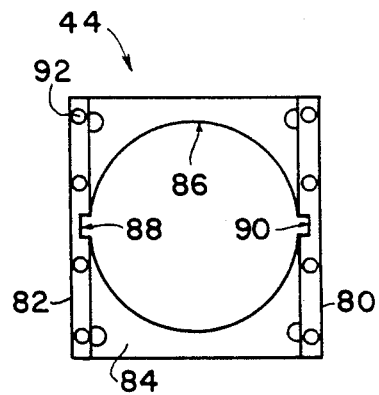
FIG. 5A is a top view of a component of the FIG. 2 embodiment.
Figure 5B:
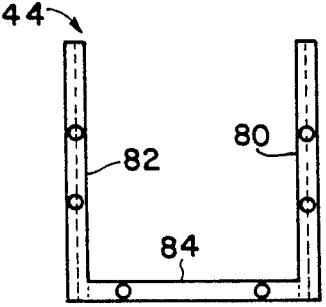
FIG. 5B is a rear view of the component of FIG. 5A.
Figure 5C:
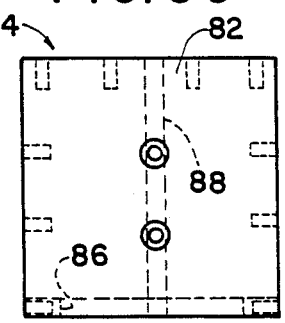
FIG. 5C is a side view of the component of FIG. 5A.

FIGS. 5A, 5B, and 5C illustrate the cage 44 having side walls 82 and 84 and a rear wall 84. The rear wall 84 has an opening 86 corresponding to the mounting position of the permanent magnet 72. Grooves 88 and 90 are provided in the side walls 80 and 82, respectively, for receiving the stationary plate 76. A plurality of holes 92 are provided for assembly purposes, and receive threaded fasteners (not shown).

Figure 6A:
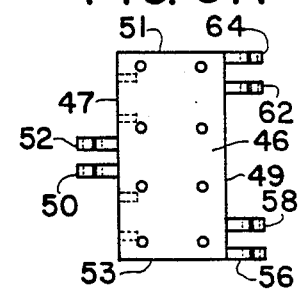
FIG. 6A is a top view of another component of the FIG. 2 embodiment.
Figure 6B:
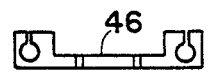
FIG. 6B is a side elevation view of the component of FIG. 6A.

Referring to FIGS. 6A and 6B, upper moving plate 46, which is identical of lower moving plate 48, has a plurality of holes 94 for mounting components thereto. Each plate has opposite sides 47 and 49 and opposite ends 51 and 53. Brackets 50 and 52 are formed at the center of side 47. Brackets 62, 64 and 56, 58 are formed at opposite ends of side 49.

Figure 7A:
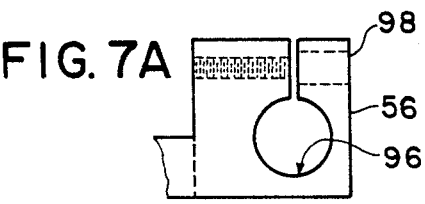
FIG. 7A is an enlarged, side elevation view of a portion of the component of FIG. 6A.
Figure 7B:
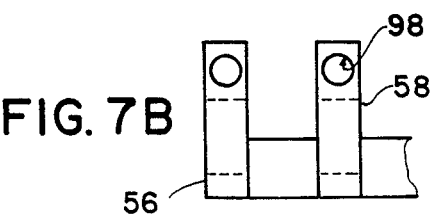
FIG. 7B is a front view of the enlarged portion illustrated in FIG. 7A.

FIGS. 7A and 7B illustrate details of brackets 56 and 58. Each bracket has a transverse hole 96 for mounting a flexure pivot. The hole diameter, and thus the friction between the hole 96 and each corresponding flexure pivot, is adjustable by means of a threaded fastener (not shown) receivable in hole 98.

Figure 8A:
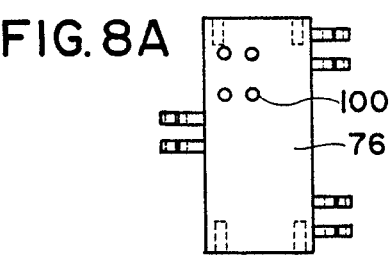
FIG. 8A is a top plan view of another component of the embodiment of FIG. 2.
Figure 8B:
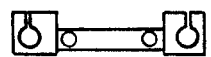
FIG. 8B is a side elevation view of the component of FIG. 8A.

FIGS. 8A and 8B illustrate the stationary plate 76 which is also provided with holes 100 for mounting components.

Figures 9A, 9B:
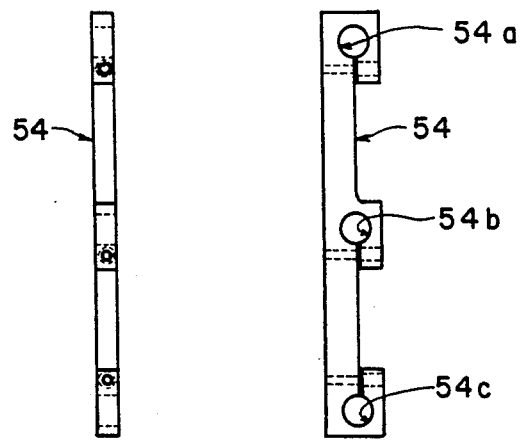
FIG. 9A is a top plan view of another component of the FIG. 2 embodiment.
FIG. 9B is a side elevation view of the component of FIG. 9A.

Referring to FIGS. 9A and 9B, one of the three links, link 54, has holes 54a, 54b and 54c provided in one end portion, a medial portion, and an opposite end portion, respectively. Hole 54a is concentrically aligned with the holes 96 of brackets 50 and 52 provided on each of the upper and lower moving plates and the stationary plate. A flexure pivot 70 passes through the aligned holes and provides a friction free pivotal connection between the link 54 and the various plates.

Figure 10:
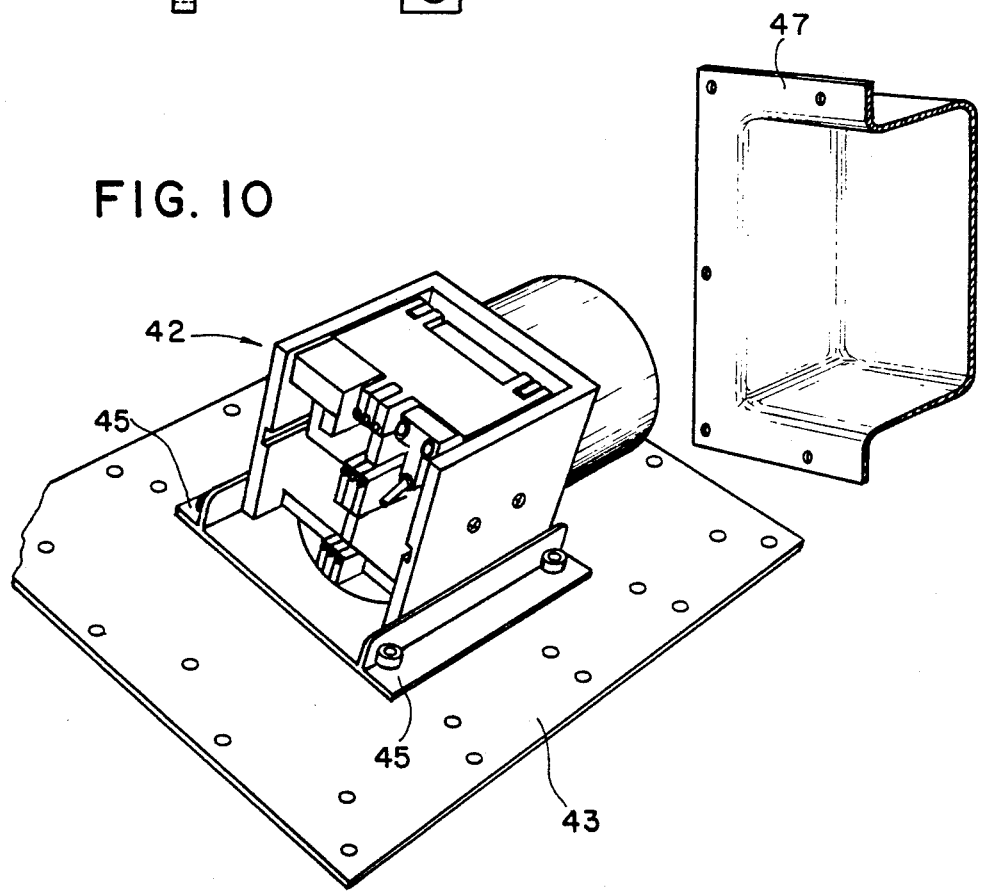
FIG. 10 is a perspective view of the FIG. 2 embodiment.

FIG. 10 illustrates in a perspective view the assembled skin friction balance 42 positioned on a mounting plate 43 and supported by mounting brackets 45. A casing 47 is mounted over the mounting plate 43 to seal the balance 42 from an interior of the aircraft in which the balance 42 is mounted. Connection of the mounting plate, mounting brackets 95, and the mounting plate 43, is made by any conventional means.

The parallel linkage mechanism 78 is kept in a null position by the force motor 75, which is part of a servo-mechanism controlled by a closed-loop control system. Basically, control is affected by comparing a desired value to an actual value, and the difference (or error) between them is then used to bring the actual value closer to the desired value. The use of a closed-loop control maintains a constant gap size during operation.

The block diagram of FIG. 11 represents the control system which operates the parallel linkage mechanism 78. A null position is achieved when the restoring force generated within the force motor is equal to the applied skin friction force. This is achieved by using an integrator, as illustrated schematically in FIG. 12. The servo circuit 108 includes a servo which is made of operational amplifiers. The servo is used to process the displacement signal received from the LVDT 102. A first operational amplifier 110 provides the integral-plus-proportional control action required to meet the type 1 closed-loop systems specification of the present control system. A second operational amplifier 112 supplies band-limited differentiation on the LVDT signal in order to obtain the desired damping characteristics required for proper operation of the system. A third operational amplifier 114 removes or nulls the LVDT bias. Each of the operational amplifiers 110, 112, and 114 includes a low-pass filter for reducing noise. The processed LVDT signal from the servo is fed to a power amplifier 116 to supply the appropriate amount of current to the motor coil required for nulling. A measurement of the subsequent voltage drop in the motor coil circuit serves as an output signal indicative of the amount of skin friction.

The power amplifier 116 is made up of a buffer amplifier and an operational amplifier and is capable of supplying up to ±100 mA of direct current to the motor coil winding. The balance output voltage is obtained from the voltage drop across a fixed resistor placed in series with the motor coil. Different full scale outputs can be obtained by changing the fixed resistor. The operational amplifiers 110, 112, and 114 of the servo are general purpose operational amplifiers. Characteristics of the servo can be readily changed by varying the RC components of the feedback and/or feed-forward paths.

A signal conditioner 118 is external to the servo or balance control circuit 108 and includes a plurality of operational amplifiers. Basically, the signal conditioner 118 provides low-pass filtering, ranging, and offset changes. Adjustments in the servo provide the overall gain for an optimal closed-loop operation. Basically, the system is a type-one closed-loop system with five open-loop poles and two open-loop zeros.

Experimental results using a prototype of the present invention demonstrate that the control system illustrated in FIGS. 11 and 12 coupled to the parallel linkage mechanism achieves a 0.5 second settling time. In bench tests, step inputs were applied to the balance to establish the dynamic characteristics thereof. The system was found to have approximately a 10% overshoot when the bandwidth of the system was set at about 250 radians per second. It should be noted that the low-pass filters used in the control circuit are needed to suppress the noise resulting from the band-limited differentiator. The cut-off frequency of the filter could be lowered to improve the noise reducing capability of the system if a longer settling time or lower bandwidth could be tolerated. Moreover, the control system is designed such that overall gain can be doubled with negligible loss of relative stability. Gain change of the control circuit can be easily realized by varying the total resistance of the motor coil circuitry. For example, if the coil resistance is halved, the full scale value of the balance will be doubled.

The many features and advantages of the present invention are apparent from the detailed specification, and thus, it is intended by the appended claims to cover all such features and advantages of the skin friction balance which fall within the true spirit and scope of the invention. Further, since numerous modifications and changes will readily occur to those skilled in the art based upon the disclosure herein, it is not desired to limit the invention to the exact construction and operation illustrated and described. Accordingly, all suitable modifications and equivalents may be resorted to falling within the scope and the spirit of the invention.

What is claimed is:

1. A skin friction balance comprising:
   a parallel linkage mechanism including a housing having two opposite sides, a stationary plate having two opposite sides and two opposite ends and being fixedly mounted by the two opposite ends thereof between the two opposite sides of the housing, at least one link pivotally connected to each of the two opposite sides of the stationary plate, each link having a center and two opposite ends, the stationary plate being pivotally connected at the center of each link, an upper movable plate pivotally connected to one of the two ends of each link, a lower movable plate pivotally connected to the opposite of the two ends of each link;
   a sensing element fixedly connected to the upper movable plate and being movable with the upper movable plate in response to sensed skin friction;
   a linear variable differential transformer outputting a signal indicative of a position of the sensing element and having a body connected to the stationary plate and an armature movable in response to movement of the lower and upper movable plates;
   a motor having a magnet fixedly connected to the housing and coil windings fixedly connected to the lower movable plate; and
   control means for processing the transformer signal and for outputting a nulling current to the coil windings of the motor at a level sufficient to maintain the sensing element in a null position, the current level being indicative of skin friction.

2. A skin friction balance according to claim 1, further comprising flexure pivot means for pivotally connecting each link to the upper and lower movable plates and the stationary plate.

3. A skin friction balance according to claim 2, wherein the at least one link comprises a first link pivotally connected in the middle of one side of the upper and lower movable plates and the stationary plate, a second link pivotally connected at one end of the opposite side of the upper and lower movable plates and the stationary plate, and a third link pivotally connected at the opposite end of the opposite side of the upper and lower movable plates and the stationary plate.

4. A skin friction balance according to claim 1, wherein the armature of the transformer is connected to the lower movable plate.

5. A parallel linkage mechanism for a skin friction balance, comprising:
   a housing having two opposite sides;
   a stationary plate having two opposite sides and two opposite ends and being fixedly mounted by the two opposite ends between the two opposite sides of the housing;
   at least one link pivotally connected to each of the two opposite sides of the stationary plate, each link having a center and two opposite ends, the stationary plate being pivotally connected at the center of each link; and
   an upper movable plate pivotally connected to one end of each link;
   a lower movable plate pivotally connected to the opposite end of each link.

6. A parallel linkage mechanism according to claim 5, wherein the two opposite sides of the housing are each provided with a groove into which the opposite ends of the stationary plate are mounted.

7. A parallel linkage mechanism according to claim 5, wherein the at least one link comprises a first link pivotally connected in the middle of one side of the upper and lower movable plates and the stationary plate, a second link pivotally connected at one end of the opposite side of the upper and lower movable plates and the stationary plate, and a third link pivotally connected at the opposite end of the opposite side of the upper and lower movable plates and the stationary plate.

8. A parallel linkage mechanism according to claim 7, further comprising flexure pivot means for pivotally connecting each link to the upper and lower movable plates and the stationary plate.

9. A parallel linkage mechanism according to claim 8, wherein each flexure pivot means comprises two parallel, spaced apart brackets extending outwardly from the upper and lower movable plates and the stationary plate, a space between the two brackets receiving an end of one of the links, the ends of the links and the brackets being provided with transverse holes which are axially aligned, and a flexure pivot extending between the two brackets through the holes of the links.

* * * * *